US012616419B2

(12) United States Patent
Reiner

(10) Patent No.: US 12,616,419 B2
(45) Date of Patent: May 5, 2026

(54) STRUCTURALLY DYNAMIC AND RECONFIGURABLE SMART MEDICAL DEVICES

(71) Applicant: Bruce Reiner, Berlin, MD (US)

(72) Inventor: Bruce Reiner, Berlin, MD (US)

( * ) Notice: Subject to any disclaimer, the term of this patent is extended or adjusted under 35 U.S.C. 154(b) by 350 days.

(21) Appl. No.: 18/362,619

(22) Filed: Jul. 31, 2023

(65) Prior Publication Data

US 2023/0380765 A1     Nov. 30, 2023

Related U.S. Application Data

(63) Continuation-in-part of application No. 17/836,742, filed on Jun. 9, 2022, which is a continuation-in-part of application No. 17/712,693, filed on Apr. 4, 2022, now Pat. No. 11,974,861, and a continuation-in-part of application No. 17/575,048, filed on Jan. 13, 2022, now Pat. No. 11,801,011, said application No. 17/712,693 is a continuation of application No. 16/503,920, filed on Jul. 5, 2019, now Pat. No. 11,324,451, which is a continuation-in-part of application No. 15/632,817, filed on Jun. 26, 2017, now abandoned, said application No. 17/575,048 is a
(Continued)

(51) Int. Cl.
| | |
|---|---|
| *A61B 5/00* | (2006.01) |
| *A61B 5/07* | (2006.01) |
| *A61B 34/30* | (2016.01) |
| *A61B 1/04* | (2006.01) |
| *A61B 10/04* | (2006.01) |
| *A61B 90/00* | (2016.01) |

(52) U.S. Cl.
CPC .............. *A61B 5/6861* (2013.01); *A61B 5/07* (2013.01); *A61B 34/30* (2016.02); *A61B 1/041* (2013.01); *A61B 10/04* (2013.01); *A61B 2034/303* (2016.02); *A61B 2090/3983* (2016.02); *A61B 2562/0285* (2013.01)

(58) Field of Classification Search
CPC ... A61B 5/6861; A61B 1/00016; A61B 1/041; A61B 34/30; A61B 2034/303; A61B 2562/0285
See application file for complete search history.

(56) References Cited

U.S. PATENT DOCUMENTS

| | | |
|---|---|---|
| 5,596,988 A | 1/1997 | Markle et al. |
| 9,320,465 B2 | 4/2016 | Kline |

(Continued)

OTHER PUBLICATIONS

Non-Final Office Action issue in U.S. Appl. No. 15/434,783, filed Oct. 3, 2019.

(Continued)

*Primary Examiner* — Chu Chuan Liu
(74) *Attorney, Agent, or Firm* — Edwards Neils LLC; Jean C. Edwards, Esq.

(57) ABSTRACT

The present invention relates to fully autonomous self-navigational medical devices which can be transported within a host subject without existing physical constraints, including those of current physical force limitations, and which are free to undergo a variety of structural and functional adaptations including the ability to perform real-time dynamic adjustment and adaptability to ever changing physiologic, anatomic, and pathologic conditions within the host subject.

20 Claims, 5 Drawing Sheets

Related U.S. Application Data continuation of application No. 15/434,783, filed on Feb. 16, 2017, now Pat. No. 11,224,382.

(60) Provisional application No. 63/422,616, filed on Nov. 4, 2022, provisional application No. 63/394,823, filed on Aug. 3, 2022, provisional application No. 62/694,248, filed on Jul. 5, 2018, provisional application No. 62/355,031, filed on Jun. 27, 2016, provisional application No. 62/295,787, filed on Feb. 16, 2016.

(56) References Cited

U.S. PATENT DOCUMENTS

| | | | |
|---|---|---|---|
| 9,895,103 | B2 | 2/2018 | Hyde et al. |
| 10,959,878 | B2 | 3/2021 | Wolfertz et al. |
| 2002/0111535 | A1* | 8/2002 | Kim ..................... A61B 1/041 600/158 |
| 2010/0198048 | A1 | 8/2010 | Togawa |
| 2016/0029952 | A1 | 2/2016 | Hunter |
| 2016/0135668 | A1* | 5/2016 | Gat ....................... A61B 1/041 600/118 |
| 2017/0020422 | A1 | 1/2017 | Bigelow et al. |
| 2017/0068792 | A1 | 3/2017 | Reiner |
| 2017/0119278 | A1 | 5/2017 | Hyde et al. |
| 2020/0375682 | A1* | 12/2020 | Kincaid ................. A61B 34/20 |

OTHER PUBLICATIONS

Non-Final Office Action issue in U.S. Appl. No. 15/434,783, filed Jul. 13, 2020.

Non-Final Office Action issue in U.S. Appl. No. 15/434,783, filed Apr. 13, 2021.

K. Ogawa et al.; "On-chip internalization process of an intracellular nanobot into a single cell"; 2017 IEEE 30th International Conference on Micro Electro Mechanical Systems (MEMS); 2017, pp. 581-584, doi: 10.1109/MEMSYS.2017.7863473. (Year: 2017).

M. Pourhomayoun et al.; "Accurate Localization of In-Body Medical Implants Based on Spatial Sparsity"; IEEE Transactions on Biomedical Engineering, vol. 61, No. 2, pp. 590-597, Feb. 2014, doi: 10.1109/TBME.2013.2284271. (Year: 2014).

J. Li et al; Micro/nanorobots for biomedicine: Delivery, surgery, sensing, and detoxification. Science Robotics, 2(4), eaam6431; https://doi .org/10.1126/scirobotics.aam6431 (Year: 2017).

Non-Final Office Action issued in U.S. Appl. No. 16/503,920, filed Oct. 7, 2021.

* cited by examiner

STRUCTURALLY DYNAMIC AND RECONFIGURABLE SMART MEDICAL DEVICES

CROSS-REFERENCE TO RELATED APPLICATIONS

The present invention claims priority from U.S. Provisional Patent Application Nos. 63/422,616 filed Nov. 4, 2022, and 63/394,823 filed Aug. 3, 2022, and is a Continuation-in-Part (CIP) of U.S. Nonprovisional patent application Ser. No. 17/836,742 filed Jun. 9, 2022, U.S. Nonprovisional patent application Ser. No. 17/712,693 filed Apr. 4, 2022, and U.S. Nonprovisional Ser. No. 17/575,048 filed Jan. 13, 2022, the contents of all of which are herein incorporated by reference in their entirety.

BACKGROUND OF THE INVENTION

1. Field of the Invention

The present invention relates to fully autonomous self-navigational medical devices which can be transported within a host subject without existing physical constraints, including those of current physical force limitations, and which are free to undergo a variety of structural and functional adaptations including the ability to perform real-time dynamic adjustment and adaptability to ever changing physiologic, anatomic, and pathologic conditions within the host subject.

2. Description of the Related Art

In current practice, in vivo medical devices are positioned into the host subject by either traditional invasive techniques (e.g., surgery) or percutaneously, using minimally invasive techniques (e.g., coronary artery catheterization). Minimally invasive device placement is generally preferred due to reduced patient morbidity and recovery time. The disadvantage of minimally invasive device placement is that it is both operator, patient, and technology dependent.

Patient dependence is often determined by patient clinical status, body habitus, and ability to follow commands. At the same time, a patient's underlying pathology (e.g., arterial occlusive disease) will often serve as a determining factor in procedural success or failure. Simply stated, when device placement involves inherent deficiencies in the operator and/or patient, success is far from guaranteed and may incur high rates of iatrogenic complication (e.g., bleeding, tissue injury). When any one of these factors is deficient, the end result may be suboptimal.

For minimally invasive vascular catheter placement, the operator (which can be human or robotic), routinely makes a skin incision through which the device (e.g., catheter) and guidewire will be inserted. Guidewires are metallic wires which facilitate the passage of the catheter, which on its own, would be limited due to physical constraints. The components of guidewires include an inner core made of stainless steel or nitinol, an outer body made of coils or polymers, a distal flexible tip made of platinum or tungsten alloy, and a surface coating.

The passage of the vascular catheter is determined by two often opposing forces, pushability and navigation. Pushability refers to the force required to advance the catheter to its designated site, while navigation refers to the ability of the catheter to move freely through a non-linear pathway like the vascular system. One can see that these forces of pushability and navigation often act in opposition to one another, creating challenges for minimally invasive device placement.

Thus, in order to advance the catheter, sufficient push force must be exerted by the operator to overcome the friction forces between the outer surface of the catheter shaft and the interior vessel wall. For devices introduced using currently available minimally invasive techniques, device maneuverability and steering capabilities are limited by torque and the frictional forces between the catheter and blood vessel walls, as defined by Euler-Bernoulli beam and Cosserat rod theories. As the catheter advances and vascular surface contact increases, the push force must also increase in order to continue advancement of the catheter. Using conventional push-pull and twisting techniques, the operator will attempt to maneuver the device, often incurring damage to the vessel. Further, as these push forces increase, the catheter shaft is prone to buckle and kink, which impedes successful placement. Thus, it is common for underlying vascular tortuosity and/or obstruction to prevent successful navigation, even in the hands of an experienced and technically proficient operator (where a successful outcome is often dictated by the individual skills, expertise, and experience of the operator).

A number of technical developments in catheter design and construction have been created in an attempt to address these challenges. For example, the tendency to kink can be addressed by a variety of structural modifications including increased catheter shaft diameter, wall thickness, and flexural modulus of the catheter shaft material (which is the ability of the material to bend).

Further, reducing catheter shaft diameter, wall thickness, and flexural modulus can improve catheter flexibility and navigation, so that the catheter shaft remains flexible in order to easily bend to accommodate to the curvature of the blood vessel in which it travels, without causing traumatic injury.

These design improvements include (but are not limited to) improvements in shaft materials (e.g., high-consistency silicone rubbers (HCR) and liquid silicone rubbers (LSR), reduction of vascular friction through hydrophilic catheter coatings, segmented catheter design, use of nano clays for polymer reinforcement, and creation of manually steerable catheters.

While a number of physical improvements have been made in catheter composition and design, these advancements are ultimately constrained by the guidewire system and manual forces used for device transport. As long as these factors remain, the evolution of medical devices will remain in a relatively limited state, and in spite of these advancements, minimally invasive catheter placement remains problematic and as previously stated, is often operator and patient dependent.

Further, in accordance with existing medical device technology, a number of physical constraints limit the adaptability and evolution of in vivo medical devices. These constraints are tied to a variety of limiting factors related to the operator, host subject, physical environment in which the device is deployed, required functionality of the device, as well as the methods used for device introduction and transport.

In fact, current medical devices have been fixed and static in structure and design. In large part due to the physical constraints placed upon medical devices by current insertion and navigation techniques, medical devices enter the host subject in their final form, and travel in that form to their designated site where they will perform their duties.

Whether it is a cardiac pacemaker, intravascular filter, central venous catheter, or biliary stent; the device structure, composition, and components currently remain static and fixed in configuration and structure. But this inability to adapt and modify to the ever-changing milieu in which they must travel, and function ultimately limits their anatomic reach and functionality.

The present invention provides a new approach to medical device placement which addresses many of the existing pitfalls and challenges intrinsic to conventional practice.

SUMMARY OF THE INVENTION

The present invention relates to fully autonomous self-navigational medical devices which can be transported within a host subject without existing physical constraints, including those of current physical force limitations, and which are free to undergo a variety of structural and functional adaptations including the ability to perform real-time dynamic adjustment and adaptability to ever changing physiologic, anatomic, and pathologic conditions within the host subject.

In one embodiment, the present invention relates to a medical device for use in vivo, including: a device body; at least one sensor disposed in the device body, to receive and/or transmit real-time data; wherein the at least one sensor detects an obstruction to a path of the device body to a predetermined destination in vivo based on the data; and a configuration mechanism which utilizes the data and based on an analysis of the data, changes a configuration of the medical device including at least one of a structural integrity, a size, a shape, a consistency or a flexibility of the medical device to allow navigation of the medical device past the obstruction to the path of the medical device.

In one embodiment, the medical device is capable of being disassembled into constituent individually operable parts and reassembled into an original configuration.

In one embodiment, the medical device further includes a camera located at one end of the device body; wherein the camera and the at least one sensor are positioned at least at one end of the device body.

In one embodiment, the medical device is a catheter.

In one embodiment, the configuration mechanism includes one of a programmable material or a programmable object in the device body which changes the at least one of structural integrity, size, shape, consistency or flexibility of the medical device.

In one embodiment, the configuration mechanism is activated by one of a first triggering mechanism or a first signal which actuates the at least one of programmable object or programmable material.

In one embodiment, one of the programmable material or the programmable object is made from one of self-transforming carbon fibers, programmable printed wood grains, custom composites, meta-surfaces constructed from a matrix of filamentary metal traces, programmable atom equivalents, synthetic condensates, programmable rubbers or programmable plastics.

In one embodiment, the consistency of the medical device includes one of a liquid, a gel, an elastomer, or a solid.

In one embodiment, the programmable object includes actuators that are independently activated to change the configuration of the medical device.

In one embodiment, actuators are disposed in outer walls of the catheter.

In one embodiment, a second triggering mechanism or a second signal restores the medical device to a baseline state.

In one embodiment, the outer walls contain embedded components including at least one of the at least one sensor, the camera, a computer system, a propulsion system, a drug reservoir, an injection system, or a release mechanism.

In one embodiment, an authentication process is required before the configuration mechanism is activated.

In one embodiment, the individually operable parts include one of individual segments or sub-components which can detach from the device body and navigate independently to the predetermined destination where the individually operable parts can re-attach to attain the original configuration.

In one embodiment, the individually operable parts include embedded components including at least one of the at least one sensor, the camera, a computer system, a propulsion system, a drug reservoir, an injection system, or a release mechanism.

In one embodiment, the individually operable parts include individual segments capable of independent movement from a neighboring segment.

In one embodiment, the individual segments are joined together using attachment mechanisms.

In one embodiment, the configuration mechanism reduces a diameter of the medical device.

In one embodiment, the configuration mechanism allows multiple individual medical devices to be contained with the medical device.

In one embodiment, a method of navigating an obstruction of a medical device in vivo, includes: receiving and/or transmitting real-time data from at least one sensor disposed in a device body; detecting an obstruction to a path of the medical device to a predetermined destination in vivo based on the data; analyzing the data for real-time modifications or interventions and based on the analysis of the data, changing a configuration of the medical device including at least one of a structural integrity, a size, a shape, a consistency or a flexibility of the medical device; and navigating the medical device past the obstruction of the medical device.

Thus, has been outlined, some features consistent with the present invention in order that the detailed description thereof that follows may be better understood, and in order that the present contribution to the art may be better appreciated. There are, of course, additional features consistent with the present invention that will be described below, and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

Figures 1A, 1B, 1C:
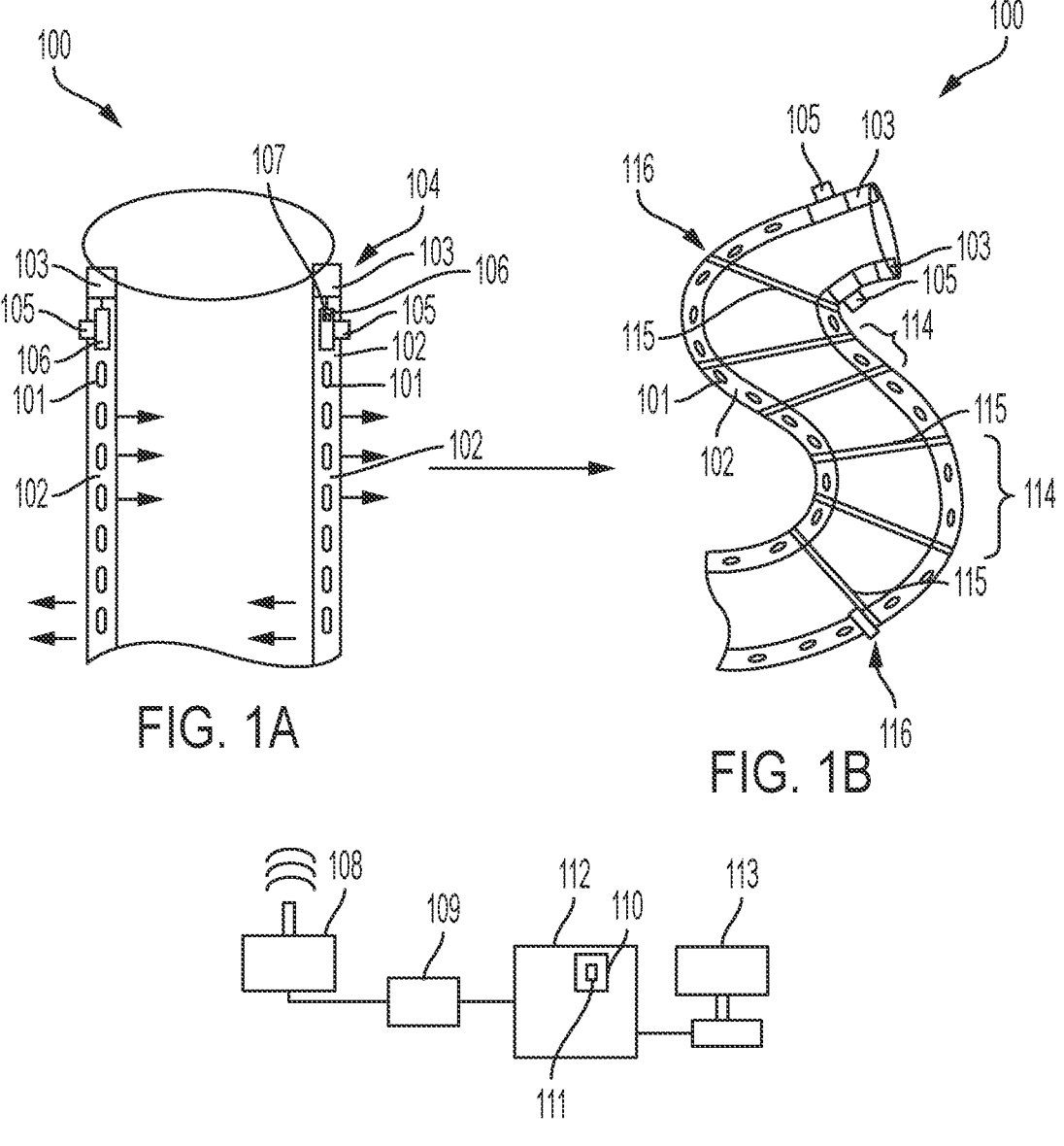
FIG. 1A is a cross-sectional side view of a smart device, such as a catheter, which shows internal programmable objects and other devices in the outer wall, according to one embodiment consistent with the present invention.
FIG. 1B shows the catheter of FIG. 1A programmed to change its configuration according to one embodiment consistent with the present invention.
FIG. 1C is a computer system that controls the operation of the catheter of FIGS. 1A and 1B, according to one embodiment consistent with the present invention.

The present invention relates to fully autonomous self-navigational medical devices which can be transported within a host subject without existing physical constraints, including those of current physical force limitations, and which are free to undergo a variety of structural and functional adaptations including the ability to perform real-time dynamic adjustment and adaptability to ever changing physiologic, anatomic, and pathologic conditions within the host subject.

While the present invention is directed to a wide array of medical devices and applications, for brevity, vascular catheters will be the focus of the examples, since they include a large percentage of medical devices in current use. When applicable, other types of medical devices will be discussed.

U.S. Provisional Patent Application Nos. 63/422,616 filed Nov. 4, 2022, and 63/394,823 filed Aug. 3, 2022, Continuation-in-Part (CIP) of U.S. Nonprovisional patent application Ser. No. 17/836,742 filed Jun. 9, 2022, U.S. Nonprovisional patent application Ser. No. 17/712,693 filed Apr. 4, 2022, and U.S. Nonprovisional No. 17/575,048 filed Jan. 13, 2022, which are hereby referred to as the "incorporated patents/applications", describe fully autonomous self-navigational medical devices which can be transported within a host subject, and include the ability to perform real-time dynamic adjustment and adaptability to ever changing physiologic, anatomic, and pathologic conditions within the host subject.

The present invention is directed to medical devices which possess the ability to undergo adaptive change in a proactive, safe and intuitive manner, and which no longer need to be fixed and static in structure and design as current medical devices.

In one embodiment, once medical devices of the present invention are provided with the capability of autonomous navigation with intrinsic propulsion capabilities, many of the existing constraints in device structure and design can be eliminated (or at least dramatically reduced). The form in which the medical device is introduced into the host subject can now be modified and reconfigured, which has the potential to enhance navigability and function.

There are varying degrees of medical device autonomy. In one extreme the device can be entirely under the external control of a skilled operator, while at the other extreme the device is completely autonomous and self-operational. In order for the latter condition to apply, the medical device of the present invention should possess intrinsic artificial intelligence capabilities, which allow it to continuously collect and analyze data, leading to an intuitive response to the real-time challenges it will inevitably experience.

In the present invention, this proactive data-driven response takes the form of self-directed navigation, and that of device structural modification. In the end, both processes complement one another to create a device which can independently navigate and undergo adaptive change in structure and form, in order to both reach its intended anatomic destination and perform its intended function.

In one embodiment, the medical device of the present invention has the ability to change its size in order to navigate to the intended site in the patient and accomplish its task. The various options for medical device modification and/or environmental changes are noted below.

a. Change in device functional size.
b. Surface structural alterations.
c. Change in device flexibility.
d. Change in device structural state.
e. Modifications in device shape and/or configuration.
f. Device disassembly or detachment of subcomponents.
g. Assembly or aggregation of multiple devices and/or components.
h. Change in surface tension and/or chemistry.
i. Interaction with local environment through endogenous or exogenous bio-mediators.
j. Producing physical change in local anatomy or pathology.
k. Facilitated transport by secondary medical device.
l. Creation of compound devices (i.e., device within a device).
m. Incorporation of artificial muscles into device walls for optimizing steerage.

The above options for medical device modification and/or environmental changes of the present invention list a number of ways in which a medical device can undergo adaptive change to either its own internal structure or to that of the local environment in which it resides, for the purpose of improved maneuverability, navigation, and/or performance. Since a given device is only as valuable as its ability to navigate to its intended location, having the ability of devices to proactively adapt to navigational impediments can ultimately determine success or failure in its ability to carry out its intended actions.

In order to illustrate how these medical device modifications can be implemented, a few exemplary embodiments are herein presented which encompass the above medical device modification and/or environmental changes.

A. Change in Device Size

In the first exemplary embodiment, a catheter is being introduced from a peripheral location (e.g., antecubital fossa), with an intended final anatomic position within the superior vena cava. In order to reach this intended position, it must first travel through the brachial, axial, and subclavian veins. But in this case, a 60% luminal narrowing (i.e., stenosis) of the subclavian vein prevents catheter passage. While one solution might be to select a catheter of smaller size, this smaller catheter may not be capable of performing the intended function (e.g., chemotherapy infusion), which requires a minimum size for effectiveness.

An alternative option would be to utilize the catheter of the present invention, where the catheter has the ability to reduce its functional size, so it can safely pass through the point of vascular obstruction. Once safe passage has been successfully accomplished, the catheter of the present invention would also possess the ability to return to its original size so that it can complete its intended function.

More particularly, since the determining factor in catheter size for traversing the point of obstruction is its diameter, the catheter is manipulated for size reduction. In one embodiment, to reduce the catheter's diameter, the catheter is elongated or lengthened, which in turn reduces its diameter—a feature which is not available in current clinical practice and device technology.

In this exemplary embodiment of the invention, the smart device (e.g., vascular catheter) can undergo an internal change in its internal structure or composition in order to effectively reduce its diameter. One way of doing this is to change the inner consistency of the catheter, which will allow it to reconfigure itself in the desired fashion.

This can be accomplished by creating an inner core of the catheter 100 (see FIG. 1A) which is capable of changing its material structure or consistency through a triggering mechanism or signal (e.g., thermal, electrical, magnetic, chemical, light, electromagnetic), which actuates a programmable object 101 (i.e., programmable nanobot) or programmable material 102 within the catheter 100 walls, the programmable objects/materials being made from structures such as self-transforming carbon fiber, programmable printed wood grain, custom composites, metasurfaces constructed from a matrix of filamentary metal traces, programmable atom equivalents, synthetic condensates, programmable rubbers/plastics, etc.

In one embodiment, the medical device or catheter 100 of the present invention includes a computer 106, with an internal memory 107, which runs a software program and is connected to a sensor or camera 103, and which may command the programmable material 102 or programmable object 101 via the triggering mechanism (above).

In other words, in this exemplary embodiment, the vascular obstruction may be noted by the smart device 100 via a number of methods, such as by a camera or sensor 103 located at the catheter tip 104, or by the user noting the obstruction visually on an external computer display 113. Further, in one embodiment, the vascular obstruction is noted visually by the camera or sensor 103, or by sensing (i.e., pressure etc.) by the programmable material 102 or programmable object 101 of the catheter 100, and the program sends a signal from a transmitter 105 on the device/catheter 100 to the internal computer 106 or external computer 112 (via signal receiver/transmitter 108 and controller 109—see FIG. 1C), that a change is needed to the material structure (i.e., programmable object 101 and/or programmable material 102) to reduce the diameter to a size calculated by the program, so that the catheter 100 can navigate past the obstruction.

Once the program (at internal microprocessor 106 with memory 107, and/or external microprocessor 110 with memory 111) has analyzed the signal, the obstruction is analyzed by the program and visualized on the display 109, the program will trigger a signal via transmitter/receiver 105 (or from transmitter/receiver 108, which is received at receiver 105 and re-transmitted), which will instruct the programmable object 101 or programmable material 102 to change its structure or consistency of the inner core of the catheter 100 between its present configuration or consistency to one of a variety of consistencies (e.g., liquid, gel, elastomeric, solid) or sizes, based on the programmability of the object or material used for the structure itself, in order to navigate past the vascular obstruction.

In one exemplary embodiment which illustrates this action, the muscle-like actuators or programmable objects 101 within the outer device 100 walls can be independently activated (see FIG. 1B) to contract, bend, or expand, in different directions, over a wide range of magnitude. As shown in FIG. 1B, the programmable objects 102 act in parallel within both outer walls to produce an S-shaped configuration of the catheter 100 by contracting some of the actuators at different points in the catheter 100 walls.

In one embodiment, with programmable materials 102, the same objective can be obtained by providing the appropriate signal (i.e., electrical, magnetic, etc.) to the programmable materials 102 to initiate a change in structure or size, as noted above.

Thus, in this manner, by programming the materials 102 or objects 101, the present invention can implement a change in device size, structural state, a modified device shape and/or configuration, and device flexibility.

In one embodiment, in order to safeguard against unwanted conversion, an internal security feature would require an authentication code from the user prior to the program initiating the desired change to the device (i.e., catheter 100). At a later point in time, when the navigational obstruction has been bypassed, as determined by the program, a second triggering mechanism can be initiated by the program to return the inner core composition back to its original state, thereby providing the catheter 100 with the desired rigidity for routine operation.

Figure 2:
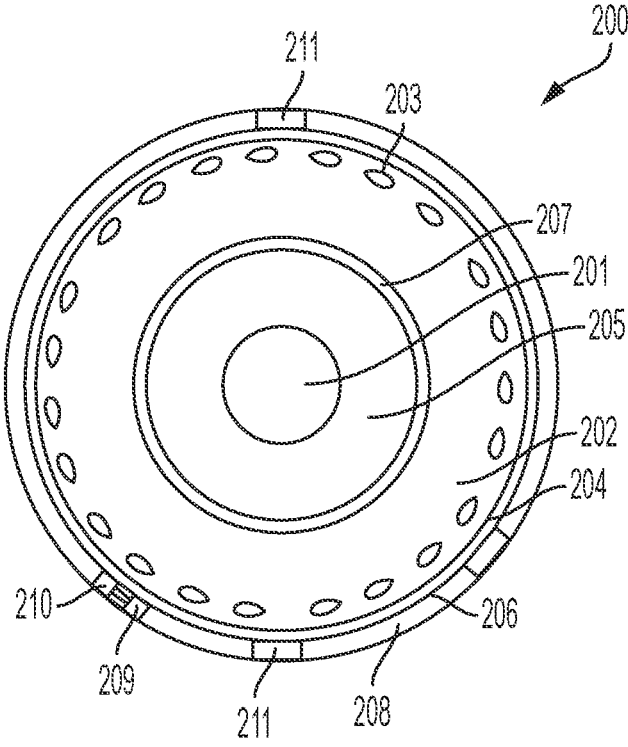
FIG. 2 is a cross-sectional end view of a smart device, such as a catheter, which shows internal programmable objects in the outer wall, according to one embodiment consistent with the present invention.

In one embodiment, in order to provide such structural diversity, the catheter 200 would include a plurality of distinct layers (see FIG. 2). For example, the central portion of the catheter 200 would represent the lumen 201. Immediately outside of the lumen 201 would be an inner core 205, and then the dynamic and reconfigurable layer 202, in which the triggering device 203 (i.e., programmable objects 203) would be located, if the outer layer 204 is not made of a programmable material.

In one embodiment, both the inner wall 207 and outer wall 206 of this reconfigurable layer 202 would be thin walls which provide support to the contents of the reconfigurable layer 202. In the outermost layer/wall 208 of the catheter 200 is a thicker solid wall which provides overall structural integrity to the catheter 200. However, one of ordinary skill in the art would know that one or more of these layers could be added/omitted depending on the desired configuration of the catheter 200 and/or the use of a programmable material instead of a reconfigurable layer 202 with activated objects 203 therein.

In one embodiment, the outermost wall 208 could contain embedded devices 211, such as sensors, computers, propulsion system (i.e., whipped tails, chemical, etc.), or cameras, etc. (see FIG. 2), which add expanded function to the smart device 200. In addition, the inner core 205 could contain materials which could undergo phase change (i.e., solid to liquid transition) to adjust the catheter elasticity, size, etc.

Further, in one embodiment, a drug reservoir 209 could be provided in the outermost wall 208, which can release a substance (e.g., liquid, gel) to the outer surface of the catheter 200 via a push mechanism 210 or other release mechanism (i.e., chemical which dissolves the reservoir barrier in the outermost wall 208 to the outside, etc.) triggered by the program, or accessed by a user via a syringe. In one embodiment, this gel would provide a surface tension reduction to allow the catheter 200 to glide across rough edges.

In one embodiment, the conversion process of the reconfigurable layer 202 can be initiated by either an authorized operator or on command of the intrinsic artificial intelligence (AI) program of the microprocessor 106/110 of the computer system 106/112. Once the conversion process has been completed, as determined by the program, in one embodiment, a second verification process can be required by the program before the internal propulsion mechanism 211 (for example) of the device 200 is activated. This provides an added level of security to ensure that the desired catheter 200 structure and compositional state is in effect before catheter 200 navigation commences.

Thus, the net effect is that internal components of the smart medical device 200 can provide the device with the ability to dynamically alter its size or change its configuration or structure, which in turn may reduce navigational challenges which might otherwise prove to be insurmountable for existing medical devices without such dynamic capabilities.

B. Alteration in Surface Structure

In one embodiment of the present invention, the smart device (i.e., catheter 200) surface structure can be altered through the emission of a chemical directly from the device outermost wall 208 (i.e., from a drug reservoir 209) which reduces the surface tension and provides for improved device navigation. In current practice, coatings are often applied to the surfaces of medical devices to prevent formation of biofilms and infection, but these have little effect on device navigability.

In the present invention, autonomous and self-navigational devices often are tasked with traversing incongruous surfaces which may serve as an impediment to safe and easy passage of the device. In one embodiment, in order to counteract this impediment is for the local release of biocompatible and absorbable chemical substances (e.g., gel, foam, viscous solution) from a drug reservoir 209, as discussed above, which can create a smooth surface which facilitates gliding action of the device 200.

As discussed in the incorporated patents/applications on smart medical devices, the architecture of smart devices was described in which a variety of miniaturized subcomponents which can be directly embedded within the device inner walls 207 and outer walls 206, 208. As described therein, reservoirs 209 containing these chemicals can be incorporated into the outermost wall 208 of smart devices 200 which can selectively release the chemicals on an as-needed basis by instructions from the program to the internal computer 106 (see FIG. 1A, for example), which can actuate release mechanisms, such as mechanism 210.

As described in the incorporated patents/applications, autonomous and self-navigating medical devices include a number of artificial intelligence (AI) technologies which provide smart devices with the innate ability to continuously detect and analyze real-time environmental conditions, some of which may necessitate proactive real-time responses by the device in order to facilitate successful navigation. Using these same AI strategies and technologies, smart devices (i.e., catheters 100) in transit may detect local environmental conditions and navigational challenges which can be best served through the release of surface altering chemicals or compounds. As described in the incorporated patents/applications on autonomous smart devices, the data recorded from these various interactions can be recorded into memory/databases 107, 111 and other external databases for the purpose of machine learning and future intervention.

In one exemplary embodiment, take the example of a smart medical device with a surface containing struts or small appendages (e.g., a cardiac stent), which could potentially damage the endothelial lining of the blood vessel in which it is travelling. In order to protect the vessel wall, drug reservoirs embedded in the device outer walls alongside the exposed struts or appendages can secrete a gel which acts to create a smooth surface along the strut surfaces, which serves to both facilitate navigation and protect the vessel wall from mechanical injury.

C. Change in Device Flexibility

While some devices will largely remain inflexible due to their construction and contents (e.g., insulin pump), other devices have greater potential for variability in structure and form (e.g., feeding tube, catheter). While conventional devices are limited in their degree of structural variation based upon the previously described physical constraints, autonomous smart devices do not share many of these constraints due to the fact that they are autonomous and capable of self-propulsion.

One manner in which medical devices can have increased flexibility (and subsequently enhanced navigation capabilities) is through articulated construction, in which the device can be subdivided into individual segments, which can function as moveable joints. If, in one embodiment, for example, a vascular catheter 100 was to be constructed into a series of articulated segments 115 (see FIG. 1B), each individual segment 114 would be capable of independent movement from its neighboring segment 114 (if each segment 114 contained its own internal propulsion capability, for example). The articulated segments 115 could be joined together using attachment mechanisms 116, including mechanical fittings or chemical glues etc.

By creating such an articulated architecture, the individual segments 114 can twist and turn independently, thereby creating enhanced device pliability and flexibility. Rather than conform to a straight-line architecture, the catheter 100 can now curve and bend in a manner that allows it to conform to the tortuous and non-linear pathway of the blood vessels and tracts in which it travels.

D. Device Disassembly and Detachment of Subcomponents

In the present invention, in addition to providing devices with the ability to increase flexibility and modify their configuration and shape, articulated device architecture also provides a unique and novel application of the present invention. In one embodiment, the individual articulated segments of the smart device possess their own intrinsic propulsion capabilities (described in the incorporated patents/applications), and thus, are able to detach themselves from the parent device and navigate independently to their intended destination site.

In one embodiment, this ability for individual device components of the present invention to detach from the core device, provides a unique ability for devices to navigate through small and confined anatomic regions, which would otherwise be non-navigable to conventional devices.

In one embodiment, this same ability to detach from the core device can also be applied to individual device subcomponents. In the incorporated patents/applications, the smart medical devices which contain embedded devices and instruments, are able to possess their own propulsion capabilities (or can be towed by another smart device or component/subcomponent). Thus, these devices and/or components/subcomponents can effectively travel independently and reunite with the parent device at the intended destination.

Figure 3A:
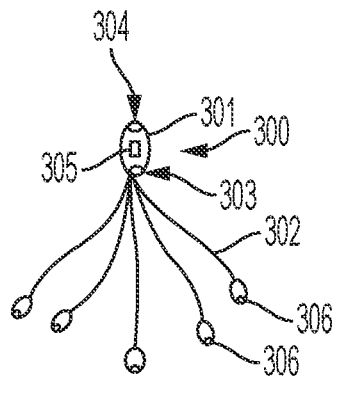
FIGS. 3A-3F are side views of a smart device, which exhibits assembly and reassembly adaptations, according to one embodiment consistent with the present invention.

In one exemplary embodiment of how a medical device can disassemble into individual components to facilitate safe in vivo navigation can be seen with the passage of an inferior vena cava (IVC) filter, as shown in FIG. 3A.

In one exemplary embodiment, an IVC filter 300 (see FIG. 3A) is constructed with a series of struts 302 attaching to a core frame 301 and having components such as a propulsion device and a directional sensor at one end 304, as well as a computer 305 (i.e., microprocessor which runs a program, a memory) disposed therein. In one embodiment, the device 300 has components at the other end 303, including a directional sensor and an attachment mechanism (i.e., hook, slot, adhesive etc.) that attaches to the struts 302 at the other end of the core frame 301.

In one embodiment, once deployed, the program instructs the struts 302 to fan out from one another to attach and fixate themselves (via hook, claw, adhesive etc.) to the walls of the IVC 300 (see FIG. 3A), by attachment mechanism 306 having positional sensors, thereby securing their permanent position. The overall size and configuration of such a medical device in its original format, creates navigational and safety challenges if one was to attempt autonomous in vivo navigation.

Figure 3B:
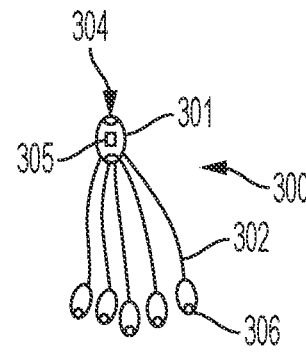

However, in one embodiment of the present invention, if the device 300 is too wide to navigate a particular obstruction, the struts 302 can be instructed by the program to collapse to a narrow diameter (see FIG. 3B), which allows the device 300 to pass through the obstruction to reach the desired position.

Figure 3C:
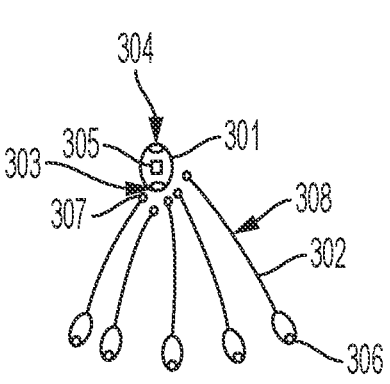
Figure 3D:
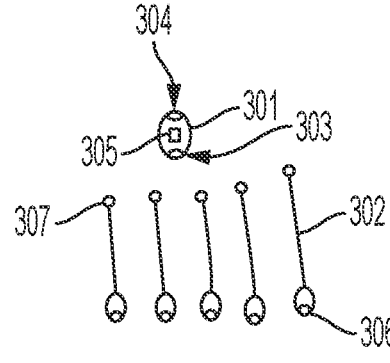
Figure 3E:
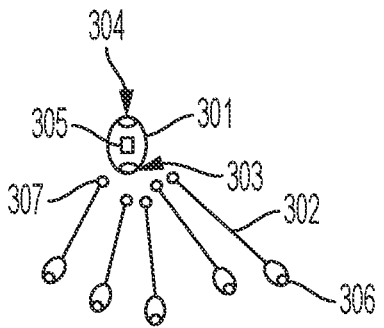
Figure 3F:
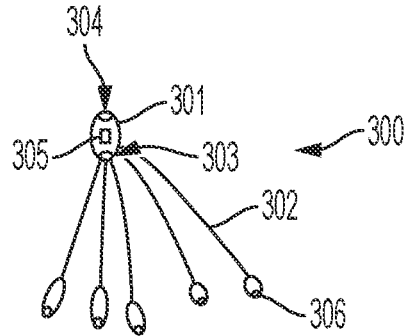

In another embodiment, if collapsing the struts 302 will not achieve the desired size to navigate an obstruction, the device 300 of the present invention circumvents this challenge by the program instructing the individual struts 302 of the device 300 to detach from the core device 301 (see FIG. 3C), by attachment mechanism (i.e., hook, slot, adhesive, etc.) at end 303 releasing the strut at end 307, to travel to the intended destination under self-propulsion based on the strut's independent propulsion device at end 307 (see FIG. 3D). Once the independent navigation has been successfully completed, the struts 302 re-attach to device body 301 using attachment mechanisms at strut end 307 and device end 303 (see FIGS. 3E-3F).

In one embodiment, if directional sensors are positioned at each end of the struts 302 at positions 307 and 306 and within the device core 301 (i.e., ends 303, 304), these could provide reference guides during the assembly process, which is analogous to coordinated assembly of jigsaw puzzle pieces.

The functionality of such an application would allow for the device 300 to be inserted in tow and then dissembled, or alternatively the individual device components to be individually inserted into the host. In either case, the individual components 301, 302 would independently navigate to the anatomic site of interest with relative ease and safety, when compared with navigation by the entire intact device 300, which would obviously have a much larger footprint.

E. Aggregation of Multiple Devices

In one embodiment, in addition to ways in which medical devices can downsize (see FIG. 3B for example) for the purpose of reducing size and structural complexity to facilitate navigation through precarious and/or confined anatomic regions, the present invention also includes dynamically changing device size and structure by upsizing.

Smart devices can come in a variety of different sizes, from microscopic nanobots to large conventional multi-faceted macroscopic smart devices. When smaller smart devices such as microbots or nanobots are in use, having the ability to merge or coalesce multiple individual devices into an aggregate multi-component smart device may create increased functionality and/or strength, which may not be available with individual smaller smart devices acting independently.

The aggregation of multiple smaller smart devices (e.g., microbots, nanobots) into a larger conglomerate in vivo smart device (i.e., macrobot) may have a number of applications. In one exemplary embodiment, an intraventricular central nervous system (CNS) tumor requiring local infusion of chemotherapy may require microscopic nanobots to cross the blood-brain barrier (BBB). However, once they cross the BBB, the small size of these nanobots limits their ability for chemotherapy delivery and infusion. If, however, one was to combine hundreds or thousands of nanobots to the task, they could have the requisite size and capacity to deliver the desired quantity of chemotherapy. In this particular example, the small size of individual nanobots is required for successful navigation to the anatomic site of interest, while the size of coalescent macrobots is required for the desired functionality.

Another exemplary embodiment where aggregation of multiple devices is advantageous is in the setting of acute trauma resulting in severe life-threatening internal bleeding. If such an event was to occur on the battlefield due to ballistic trauma, there would be insufficient time and access to conventional surgical therapy. If, however, a medic in the field was to inject a large bolus of specialized microbots or nanobots (i.e., millions), these could travel to the site of active bleeding, where they would be tasked with local administration of a blood clotting agent (e.g., thromboplastin). But if one had the capability of having these microbots or nanobots aggregate into large macrobots at the site of bleeding, they would have the combined functionality of both local chemical and physical therapeutic benefits. In addition, to localized release of the desired chemical agent, the larger size of the aggregate macrobots would produce physical occlusion of the injured blood vessels, in a manner similar to vascular coils or gel foam.

F. Local Environmental Interaction

In the present invention, smart medical devices containing a number and variety of embedded miniaturized subcomponents have both diagnostic and therapeutic capabilities. At the same time, the ability for devices to self-navigate and continuously monitor local in vivo environmental conditions is important. Thus, one would effectively have the capability of continuous real-time analysis of local environmental conditions with the ability to proactively intervene, if needed.

In an exemplary embodiment, a coronary artery catheter is tasked with navigating across an occluded coronary artery, which could be the result of a variety of pathologies including (but not limited to) atherosclerotic plaque, spasm, or intimal hypertrophy. In this exemplary embodiment, the catheter bypasses the site of obstruction by elongating itself and narrowing its effective diameter. However, the present invention also provides a number of alternative interventions, each of which can act by modifying the local environment to facilitate catheter passage across the point of obstruction. These include the following:

1. Release of chemical agents (e.g., vasodilators or thrombolytic agents) from the drug reservoir of the catheter to effectively increase luminal diameter of the vessel in question.

2. Use of subcomponents (e.g., miniaturized drills) embedded within the outer walls of the catheter to reduce plaque burden and corresponding obstruction to catheter passage.

3. Local triggering of naturally occurring bio-mediators (e.g., histamine, prostaglandins) for vasodilation via action of the appropriate glands by use of chemicals from the drug reservoir of the catheter.

Thus, in one embodiment, by increasing the functionality of smart medical devices, a number of new applications are available with the present invention, which can effectively change the local in vivo environment (as opposed to physical changes to the device alone). By doing so, the smart device becomes a dynamic instrument which can effect change both within its own internal structure as well as outside, within the local environment in which it resides.

G. Secondary Device Transport

In the present invention, a medical device can be transported by another medical device, analogous to a tugboat assisting in the navigation of a ship into a narrow harbor. In the future as smart devices become far more complex in architecture and functionality and extend to anatomic locations which may not be currently available, navigational assistance may be required. This becomes possible with the creation of autonomous device navigation.

In one exemplary embodiment, larger and more powerful transport smart devices are utilized to effectively tow or carry a smaller smart device to a target destination. In one embodiment, in order to accomplish this task, the larger transport device may have attached attachment mechanisms such as hooks, or cables, etc., which can be used to secure the smaller device for secure transit. Alternatively, in another embodiment, the smaller smart device may be positioned within the central core of the transport device and subsequently released once the target destination is reached.

Since autonomous smart devices possess the ability to self-navigate and steer, once released by the larger transport device, the smaller device in tow can then make the final leg of their intended journey through use of their own internal propulsion mechanism.

In the event that an autonomous smart device was to have its navigational system fail, the larger transport device can be dispatched to its location and effectively tow the disabled device to a site for evacuation.

H. Compound Devices (i.e., Device within a Device)

In one embodiment, another modification in device structure which can facilitate navigation and functionality is the creation of compound devices, which in effect allows multiple individual devices to be contained within a single structure. In essence, this can be thought of as a device within a device.

A number of theoretical and practical advantages arise from such a structural and compositional variation, the most important of which is the diversity and added functionality it brings to providing diagnostic and therapeutic applications to the host subject.

In one embodiment, the larger (i.e., primary) device provides a method for navigating to a shared destination site from which the smaller (i.e., secondary) device can be released. The two primary architectural options are either central or peripheral locations of the secondary device relative to the primary device.

In one embodiment, upon its release from the primary device, the secondary device can travel to its final destination site through its integrated autonomous navigation system or remain at the location in which it was deposited upon its release. Along with its ability to be released, the secondary device can also be retracted by attachment mechanisms such as hooks, cables, etc., and returned to its original positioning with the primary device.

In one embodiment, multiple smaller secondary devices can be contained within the primary device, depending upon the size and structure of the primary and secondary devices. As an example, take a smart vascular catheter which has a number of embedded subcomponents including drug reservoirs for local drug delivery. Within the core structure of this device are a number of smaller devices including a smaller-bore vascular catheter and smart vascular coils.

In one exemplary embodiment, this compound device is being used to treat a liver tumor which is located in the periphery of the liver, making it difficult to access with the larger core device. The larger device navigates as far as it can safely go into the mid right hepatic artery. From there it releases the smaller smart vascular catheter which is small enough to navigate itself to the distal hepatic artery which is supplying the tumor. Once properly positioned, it delivers a chemotherapeutic agent. Due to the small size of its drug reservoir, the amount which can be administered is less than desired. However, the larger volume drug reservoirs from the core medical device can refill the drug reservoirs of the smaller catheter, thereby infusing the complete quantity of drug (see the incorporated patents and patent applications for description of this feature).

In the exemplary embodiment, after the local drug infusion has been completed, the smart vascular coils are then released from the central core of the parent device. From there the coils navigate distally to the arterial branch supplying the tumor and embed themselves into the vascular lumen, effectively occluding the artery in the hopes that no further blood can be supplied to the tumor. Once the operation has been completed, the core device and its smaller inner catheter return to a designated site for evacuation (i.e., via retrieval etc.). This exemplary embodiment illustrates how compound devices may provide enhanced functionality and navigability beyond that available with a single smart medical device.

I. Device Steerage

Unlike traditional medical device navigation which is largely straight line in nature and limited by the requirement of an internal guidewire, the present invention and its autonomous navigational capabilities provide unique opportunities for circuitous navigation and steerage not currently available.

As stated above with respect to FIG. 1A, in one exemplary embodiment which increases the manner in which a medical device, such as a smart catheter can optimize steerage and navigability, is to incorporate or embed muscle-like actuators 101 (i.e., artificial muscles) into the device 100 walls. This provides both increased compliance and strength to the device 100 as it navigates through three basic actuation responses: contraction, expansion, and rotation, which can be combined in a single component to produce various types of motion including (but not limited to) bending, curving, contraction, and expansion. In one embodiment, these artificial muscles have the potential to be a disruptive technology due to their high flexibility, versatility, and power-to-weight ratio.

In one embodiment, artificial muscles can be divided into a number of major groups based on their actuation mechanism including (but not limited to) electric field actuation, ion-based actuation, pneumatic actuation, thermal actuation, and chemical actuation. The control of their actions can be done remotely by an authorized operator or internally through the artificial intelligence (AI) within the program of the autonomous navigational system.

In one embodiment, by embedding these artificial muscles throughout the device walls, individual and/or small groups of these muscles can be activated at any point in time to produce the desired action (e.g., bending, rotation) for a predetermined time and distance. Since the artificial muscles act independently from one another, the actions taken in one location can be distinct and separate from those actions within a different location. The net effect is that the device can twist, turn, and bend as if it was a living organism navigating through a small serpiginous space. One analogy would be that of a worm which is navigating through a narrow tunnel with twists and turns, requiring constant motion and reconfiguration.

In one embodiment, each individual muscle-like actuator can act as an independent device component and act in isolation or in combination with other muscle-like actuators. By individually controlling the actions of each actuator, complex device configurations can be achieved over short or long segments of the device. In addition, each actuator acts like an artificial muscle which can vary the strength and intensity of its actions. In one embodiment, by adjusting the magnitude of these actions, one can produce large variations in muscle response. A small magnitude contraction may result in a small bend in the adjacent device outer wall, while a higher magnitude contraction may result in a much larger bend in the device. At the same time, by recruiting nearby actuators, for similar actions, the magnitude, directionality, and length of device configuration change may be dramatically altered.

To illustrate how the invention works, the following are two exemplary embodiments, each of which utilizes a different feature of the present invention. In the first exemplary embodiment, a smart vascular catheter is inserted via the right femoral vein with the ultimate destination of the right middle cerebral artery for infusion of a thrombolytic agent in the treatment of an acute stroke. The mechanism of navigation is as described above.

In this first exemplary embodiment, upon reaching the right common carotid artery, the catheter encounters extensive atherosclerotic plaque, some of which is calcified and some of which is non-calcified and soft in nature. This soft plaque is especially worrisome because it can become easily detached and if that occurs, can freely travel downstream and cause vascular occlusion. The navigational challenge now becomes twofold. On the one hand, the catheter must travel across the 75% narrowed lumen, and at the same time, avoid dislodging soft plaque which can be catastrophic.

With the present invention, a number of options exist for addressing this challenge. In one embodiment, the functional diameter of the catheter is reduced by elongation, in which the effective diameter of the catheter is reduced by 50%. In another embodiment, the catheter releases a biocompatible gel from its outer wall, which reduces surface tension and allows the catheter to effectively glide along the path with minimal physical contact on the atherosclerotic surface of the native vessel. A yet another embodiment, the catheter changes its internal structural composition from a solid to liquid state, which renders it soft and pliable and less likely to disrupt plaque as it navigates across the diseased vessel lumen.

However, in the exemplary embodiment, once the atherosclerotic plaque within the common carotid artery has been successfully traversed, a second common obstacle is encountered. The internal carotid artery is extremely tortuous, creating an S-shaped configuration. In order to navigate through the extreme vascular tortuosity, the catheter must effectively change its configuration from that of a straight line to one with extreme curvature, mirroring the S-shape of the native vessel.

In one embodiment of the present invention, one way to accomplish this is to utilize artificial muscles (which are actually muscle-like actuators—for example, consider 101 in FIGS. 1A and 1B, as same) embedded in the catheter wall. Since these artificial muscles are positioned throughout the length of the catheter and can be activated independently, they can individually contract, elongate, and bend so that small segments of the catheter can assume a unique configuration which is distinct and separate from adjoining catheter locations. In one embodiment, if each individual muscle has the ability to titrate the degree of action taken (analogous to a programmable dial on a light switch), a spectrum exists as to the extent of catheter reconfiguration. What began as a linear configuration can now assume a myriad of shapes to accommodate to the local environment in which it finds itself.

In another embodiment, to navigate across a tortuous pathway, the present invention allows the disassembling of the native device (see FIG. 1B, for example) into smaller segments and then reattach these segments at a distant location, beyond the point of obstruction. The smaller size segments can more easily navigate across the tortuous path and can be further assisted by changing pliability through internal temperature variation.

In one embodiment, regardless of the strategy utilized, the catheter can return to its native state by simply reversing the processes it utilized to navigate across the atherosclerotic stenosis and/or tortuous pathway. The dynamic properties of the present invention provide a method which is both reversible and maintains complete functionality of the device.

In one embodiment, the decision making for device modification can be entirely internal (through the use of artificial intelligence (AI) techniques in the program) or external (through input commands from external computer system 102 or manual commands from an authorized operator.

In the second exemplary embodiment, an inferior vena cava (IVC) filter has been inserted via the right femoral vein for the purpose of trapping emboli from a right lower leg deep venous thrombosis and preventing emboli from traveling to the lungs (i.e., pulmonary emboli), which can be life threatening.

In the exemplary embodiment, a problem is encountered during the migration of the IVC filter, due to a congenital web causing narrowing of the vessel lumen. In its present form, the IVC filter is too large to pass through this focal area of narrowing and due to the complex multi-faceted structure of the device, and there is no conventional solution other than surgical placement.

With the present invention, in one embodiment, the filter can disassemble into individual parts, each of which is small enough to traverse the area of luminal narrowing (see FIGS. 3A-F). Once the destination site has been reached, these individual device components (i.e., struts 302) can be reassembled and the intact device 300 now placed at its intended anatomic position. In one embodiment, sensors embedded within each individual component at positions 307, 306 serves as aids to guide the reassembly process and a quality control test is performed prior to final deployment to ensure proper functioning of the device 300 in its entirety as well as its individual components.

In one embodiment, the individual struts 302 which serve to anchor the filter into the IVC wall can also be dynamically lengthened or shortened (e.g., using internal hydraulics 308 (see FIG. 3C, for example), to accommodate to size variability within the IVC at its implantation site. This illustrates another way in which devices 300 can be dynamically altered to adjust to the local in vivo environment.

Figure 4A:
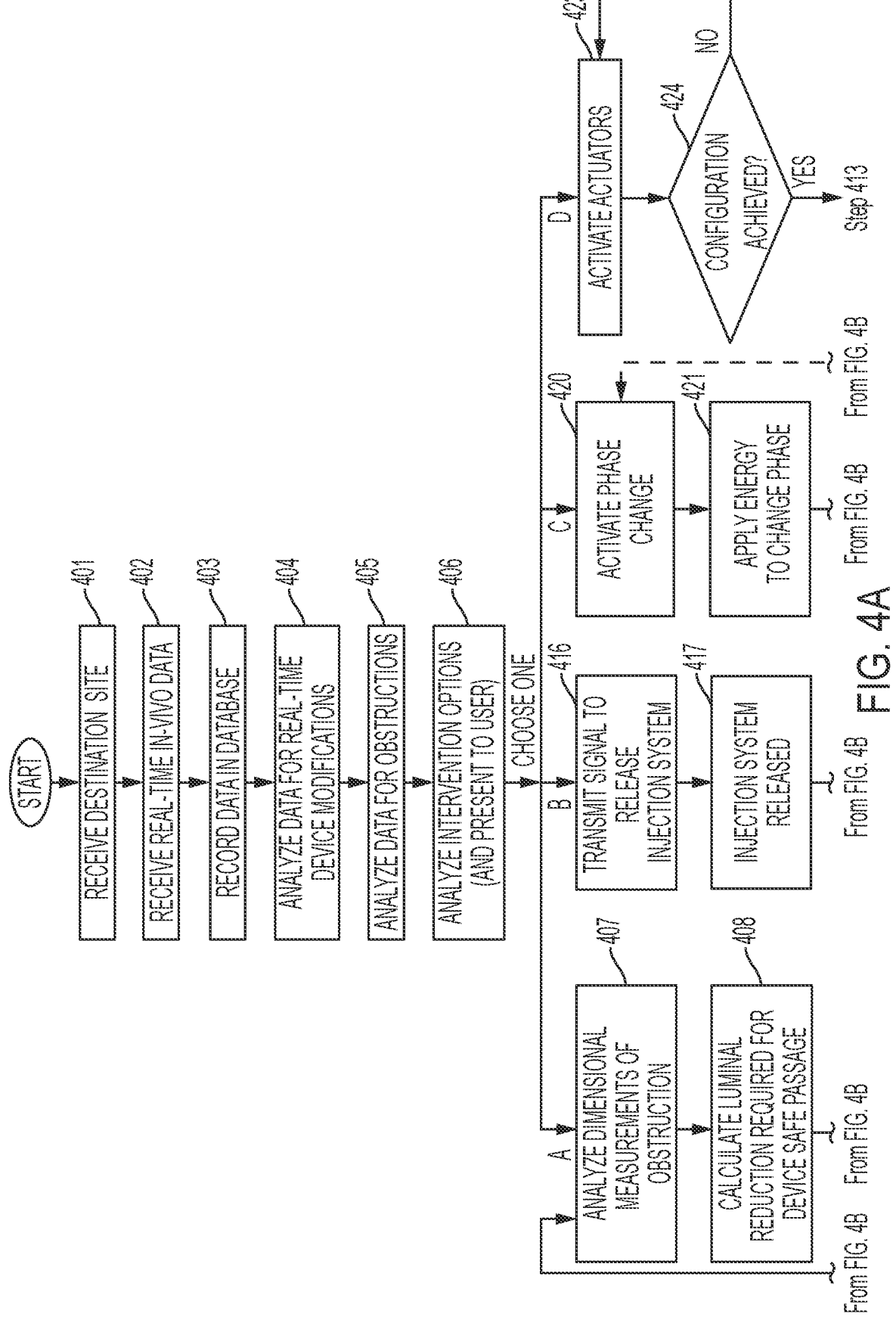
FIGS. 4A-4B is a flow chart of the steps involved in fully autonomous, self-navigation of the smart device, according to one embodiment consistent with the present invention.
Figure 4B:
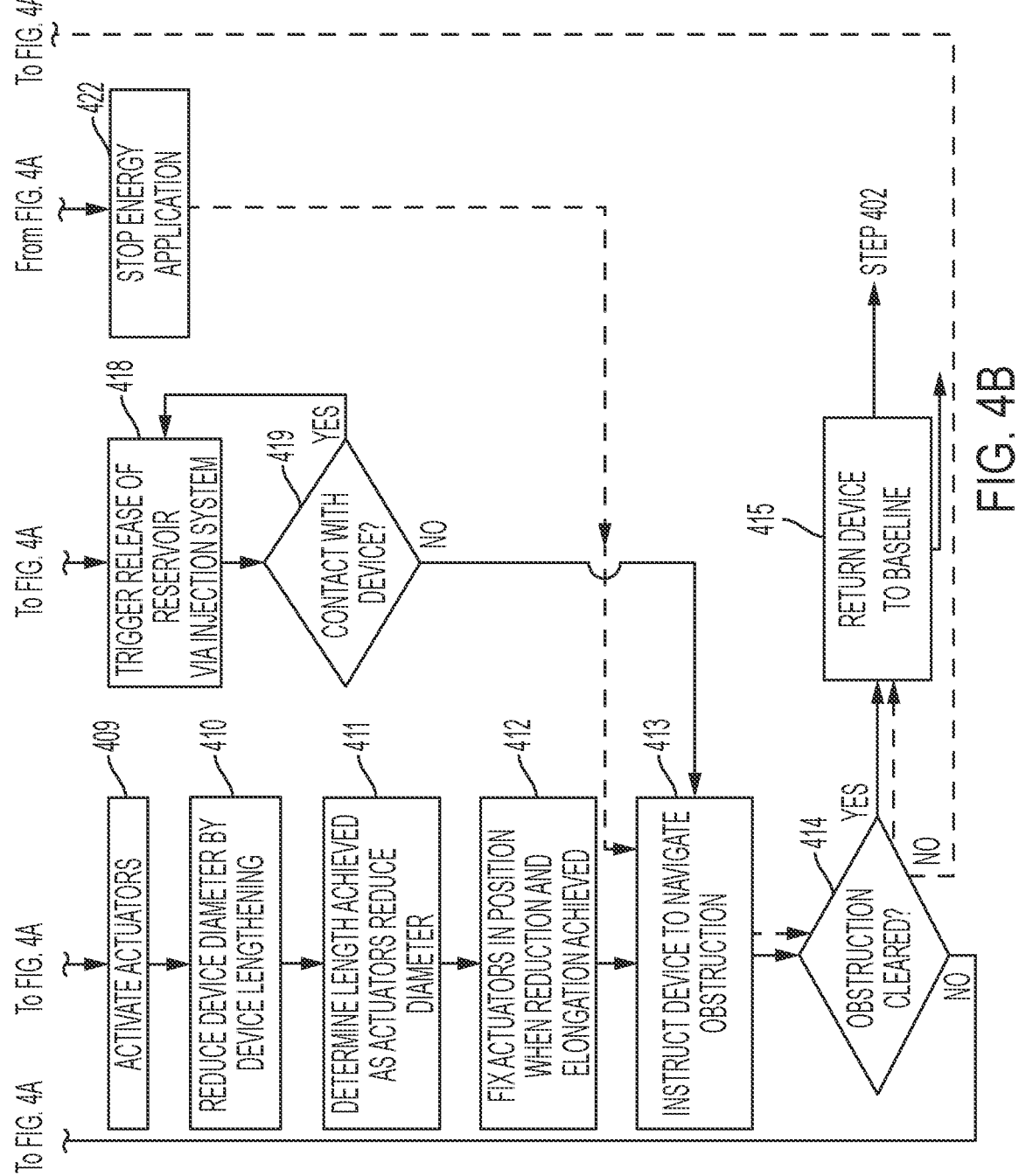

The following includes the steps for the above first exemplary embodiment, in more detail, including program method steps (see flow charts in FIGS. 4A and 4B). However, not every step is articulated and one of ordinary skill in the art would know that one or more steps should be included or omitted depending on what the user intends to accomplish.

1. Smart catheter 100 (see FIGS. 1A and 1B) is inserted into host subject.

2. Destination site programmed into smart device (catheter 100) navigation in the computer system 106 (which can operate autonomously or via external control from computer system 102/110) (Step 401).

3. Smart device embedded sensors 103 and miniaturized components (i.e., cameras) capture real-time in vivo data and transmitted to computer system 106/102 (Step 402).

4. Data being continuously collected and received by the computer system 106/102 is recorded in the database 107/111 (Step 403) and analyzed by the program for real-time device modifications (Step 404).

5. Device encounters obstruction to passage based upon device sensing or user visual observation on display 113 as analyzed by the program (Step 405).

6. Options for intervention are analyzed and reviewed by the program (Step 406) based upon available data, clinical conditions, and device architecture, and is provided by the program to user. Available options for consideration are A, B, C, and D, below, with steps involved:

A. Catheter Elongation.

A1. Data is analyzed by the program to determine dimensional measurements of vessel lumen at point of obstruction (Step 407).

A2. Calculation is performed by the program to determine the extent of luminal reduction required in order for catheter diameter to allow for safe passage of catheter across obstruction (Step 408).

A3. Muscle-like actuators (i.e., artificial muscles) embedded within walls of catheter are activated by program, causing stretching and elongation (Step 409).

A4. Activation of muscle elongation causes catheter to lengthen with subsequent reduction in diameter (Step 410).

A5. The degree of muscle stretching, and catheter elongation achieved is determined by calculation by the program of the desired luminal diameter reduction (Step 411).

A6. Once the required catheter elongation/reduction in diameter is complete, muscle-like actuators remain fixed in position (Step 412).

A7. A signal is sent to the navigational control system (either internally at computer system 106, or externally to computer system 102/110 which transmits the instruction) by the program, and the program instructs the catheter 100 to initiate passage across obstruction point (Step 413)

A8. If additional modification in catheter size is required, as determined by the program (Step 414), the process is repeated (back to Step 407).

A9. Once the obstruction is successfully navigated, the device returns to its baseline (Step 415), which includes returning the catheter 100 to its baseline dimensions by returning the muscle-like actuators to their original state.

B. Release of Biocompatible Gel from Receptacles in Device Outer Walls.

B1. The program sends signal to storage reservoirs 209 embedded within outermost wall 208 of catheter 200 (see FIG. 2) to release injection system (Step 416).

B2. A microneedle (not shown) is released from center of reservoir 209 by program (Step 417).

B3. The injection system is activated by program and gel content within the reservoir is released from catheter directly into the body via the microneedle, or into the outermost wall 208 of the catheter 200 (Step 418).

B4. In the case of the injected gel released into tracks along outermost wall 208 by the program, as catheter 200 moves, the gel forms a layer between the catheter outermost wall 208 and external environment of the body.

B5. If direct contact is made between catheter 200 and blood vessel walls, the program triggers a second release of gel from the microneedle at the specific contact point causing increased separation between the catheter outermost wall 208 and physical point of contact (Step 419). If not, the device navigates any obstruction (Step 413), and once cleared (Step 414), returns to its baseline (Step 415).

C. Change in Device Inner Composition State from Solid to Liquid for Increased Elasticity.

C1. A signal is sent by the program to activate phase change within inner core of catheter (Step 420).

C2. Upon receipt of the signal, a predetermined energy source is supplied by the program causing the desired phase change (Step 421), which in this case is from solid to liquid.

C3. Once phase change is completed to achieve the desired level of elasticity, a signal is sent by the program to cease additional energy input (Step 422).

C4. The catheter navigation system is deployed by program, instructing the catheter to navigate through the point of obstruction (Step 413).

C5. In the event that the desired level of elasticity needs to be modified to clear the obstruction (Step 414), the process is reactivated (Step 420).

C6. Once the catheter has successfully traversed the point of obstruction (Step 414), the inner core state can be returned to its baseline state by the program reversing the phase change (Step 415). The device reconfiguration can be initiated by either an authorized external operator or by the program's internal artificial intelligence (AI) program.

C8. Once intervention is completed, the program has the device resume navigation (Step 402).

D. Device Structural Modification

In all the four scenarios of the exemplary embodiments, real-time data is continuously collected and analyzed by the program to adjust modifications as needed (Steps 402-406). Further, real-time imaging data is acquired by the program to monitor structural changes and/or iatrogenic complications to native anatomy (Steps 402-406). Once any obstruction is successfully navigated, the device returns to its baseline state (Steps 413-415), and the catheter continues to navigate towards its intended destination. In this exemplary embodiment:

D1. The catheter 100 reaches a new navigational obstacle in the form of extreme vessel tortuosity (e.g., S-shaped native vessel) (Step 405).

D2. Data is collected by the program along with imagery to quantify and map the local anatomy (Step 405).

D3. Intervention options for catheter modification are provided by the program are reviewed by the user or by the program's AI computer system (Step 406).

D4. In this particular example, the program determines that the obstruction requires the catheter to change from a linear to S-shaped configuration (Step 406).

D5. In order to accomplish this structural change, muscle-like actuators embedded within the outer walls of the catheter are individually activated by the program in order to achieve the desired catheter configuration (Step 423).

D6. In this case, parallel muscle contraction is required over a length of 2.8 cm, to achieve a sharp 45-degree bend (to the left) in the catheter at its proximal end.

D7. This is followed by a program-initiated reversed 30-degree bend in the next 1.7 cm segment of the catheter to the left, requiring the corresponding wall muscles to contract in the opposite direction.

D8. The degree of contraction in each muscle-like actuator controls the extent of bending and resulting catheter curvature.

D9. This process is repeated (Step 424 to Step 423) over the length of the catheter to achieve the required configuration of the catheter across the tortuous vessel.

D10. Note the timing and specific location of muscle-like actuator activation can be carefully controlled by the program in keeping with the local environmental conditions. In some circumstances, the activation may require differential timing as the catheter navigates in a forward direction. In doing so, the reconfiguration process is dynamic in terms of catheter configurability, timing, and location.

D11. The catheter is then instructed by the program to navigate the vessel (Step 413).

D12. Once the catheter passes the point of obstruction (Step 414), it can return to its baseline state (Step 415).

Thus, the above steps are repeated until the device reaches its destination, performs its mission, and then is extracted or eliminated from the body.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A medical device for use in vivo, comprising:
a device body;
at least one sensor disposed in said device body, to receive and/or transmit real-time data;
wherein said at least one sensor detects an obstruction to a path of said device body to a predetermined destination in vivo based on said data;
a processor disposed in said device body; and
a self-propulsion device disposed in said device body;
wherein said processor utilizes said data and based on an analysis of said data, implements a change in a configuration of the medical device; and
wherein said change in configuration of the medical device includes at least one of a structural integrity, a size, a shape, a consistency or a flexibility of the medical device, such that the medical device autonomously self-navigates utilizing said self-propulsion device, said obstruction to said path of the medical device.

2. The medical device of claim 1, wherein the medical device is configured to be disassembled into constituent individually operable parts and reassembled into an original configuration.

3. The medical device of claim 1, further comprising a camera located at one end of said device body;
wherein said camera and said at least one sensor are positioned at least at one end of said device body.

4. The medical device of claim 3, wherein the medical device is a catheter.

5. The medical device of claim 4, wherein said processor actuates one of a programmable material or a programmable object in said device body which changes said at least one of structural integrity, size, shape, consistency or flexibility of the medical device.

6. The medical device of claim 5, wherein said processor implements one of a first triggering mechanism or a first signal which actuates said at least one of programmable object or programmable material.

7. The medical device of claim 6, wherein said one of said programmable material or said programmable object is made from one of self-transforming carbon fibers, programmable printed wood grains, custom composites, meta-surfaces constructed from a matrix of filamentary metal traces, programmable atom equivalents, synthetic condensates, programmable rubbers or programmable plastics.

8. The medical device of claim 4, wherein said consistency of the medical device includes one of a liquid, a gel, an elastomer, or a solid.

9. The medical device of claim 5, wherein said programmable object includes actuators that are independently activated to change said configuration of the medical device.

10. The medical device of claim 9, wherein said actuators are disposed in outer walls of said catheter.

11. The medical device of claim 6, wherein a second triggering mechanism or a second signal restores the medical device to a baseline state.

12. The medical device of claim 10, wherein said outer walls contain embedded components including at least one of said at least one sensor, said camera, a computer system, a propulsion system, a drug reservoir, an injection system, or a release mechanism.

13. The medical device of claim 1, wherein multiple individual medical devices are contained with the medical device.

14. A medical device for use in vivo, comprising:
a device body;
at least one sensor disposed in said device body, to receive and/or transmit real-time data;
wherein said at least one sensor detects an obstruction to a path of said device body to a predetermined destination in vivo based on said data; and
a processor disposed in said device body which utilizes said data and based on an analysis of said data, and implements a change in a configuration of the medical device including at least one of a structural integrity, a size, a shape, a consistency or a flexibility of the medical device, such that the medical device navigates said obstruction to said path of the medical device;
wherein an authentication process is required before said processor implements said change in said configuration.

15. A medical device for use in vivo, comprising:
a device body;
at least one sensor disposed in said device body, to receive and/or transmit real-time data;
wherein said at least one sensor detects an obstruction to a path of said device body to a predetermined destination in vivo based on said data; and
a processor disposed in said device body which utilizes said data and based on an analysis of said data, and implements a change in a configuration of the medical device including at least one of a structural integrity, a size, a shape, a consistency or a flexibility of the medical device, such that the medical device navigates said obstruction to said path of the medical device;

wherein the medical device is configured to be disassembled into constituent individually operable parts and reassembled into an original configuration; and wherein said individually operable parts include one of individual segments or sub-components which are configured to detach from said device body and navigate independently to said predetermined destination where said individually operable parts re-attach to attain said original configuration.

16. The medical device of claim 15, wherein said individually operable parts include embedded components including at least one of said at least one sensor, said camera, a computer system, a propulsion system, a drug reservoir, an injection system, or a release mechanism.

17. The medical device of claim 15, wherein said individually operable parts include individual segments which exhibit independent movement from a neighboring segment.

18. The medical device of claim 17, wherein said individual segments are joined together using attachment mechanisms.

19. A medical device for use in vivo, comprising:

a device body:

at least one sensor disposed in said device body, to receive and/or transmit real-time data;

wherein said at least one sensor detects an obstruction to a path of said device body to a predetermined destination in vivo based on said data; and a processor disposed in said device body which utilizes said data and based on an analysis of said data, and implements a change in a configuration of the medical device including at least one of a structural integrity, a size, a shape, a consistency or a flexibility of the medical device, such that the medical device navigates said obstruction to said path of the medical device;

wherein said processor implements said change in configuration to reduce a diameter of the medical device.

20. A method of navigating an obstruction of a medical device in vivo, comprising:

receiving and/or transmitting real-time data from at least one sensor disposed in a device body;

detecting an obstruction to a path of the medical device to a predetermined destination in vivo based on said data;

analyzing said data for real-time modifications or interventions and based on said analysis of said data, and changing a configuration of the medical device including at least one of a structural integrity, a size, a shape, a consistency or a flexibility of the medical device; and autonomously self-navigating using a self-propulsion device, said obstruction to said path to the medical device.

* * * * *